United States Patent [19]
Anderson

[11] Patent Number: 5,977,262
[45] Date of Patent: Nov. 2, 1999

[54] PREPARATION OF HYDROXY URETHANES

[75] Inventor: Albert Gordon Anderson, WIlmington, Del.

[73] Assignee: E. I. du Pont de Nemours and Company, Wilmington, Del.

[21] Appl. No.: 08/848,455

[22] Filed: May 8, 1997

[51] Int. Cl.[6] ..................... C07C 271/12; C07C 269/04; C08F 8/32

[52] U.S. Cl. .................. 525/327.2; 528/371; 560/157

[58] Field of Search ................ 525/327.2; 528/371; 560/157

[56] References Cited

U.S. PATENT DOCUMENTS

| | | |
|---|---|---|
| 3,072,613 | 1/1963 | Whelan . |
| 4,395,565 | 7/1983 | Romano et al. .......................... 560/24 |
| 4,882,391 | 11/1989 | Brindopke ............................. 525/327.2 |
| 5,132,458 | 7/1992 | Honel ...................................... 528/370 |

*Primary Examiner*—David Buttner

[57] ABSTRACT

The reactions of cyclic carbonates, especially 1,3-dioxolan-2-ones, with amines, especially primary amines, are catalyzed by the presence of a base whose conjugate acid has a pKa of about 11 or more. The products are hydroxy urethanes, and the process can be used to form crosslinked polymers which contain urethane groups. Such crosslinked polymers are useful in coatings.

12 Claims, No Drawings

PREPARATION OF HYDROXY URETHANES

FIELD OF THE INVENTION

Disclosed is a process for the preparation of hydroxyurethanes from amines and cyclic carbonates, catalyzed by a strong base whose conjugate acid has a pKa of about 11 or more.

TECHNICAL BACKGROUND

Cyclic carbonates, particularly cyclic carbonates containing 5-membered rings (1,3-dioxolan-2-one rings), react relatively slowly with amines, particularly at ambient (about 25° C.) temperatures. This slow reactivity has limited the usefulness of these types of reactions, for example in coatings which crosslink at ambient temperature. Therefore, means of speeding up such reactions are desired.

V. D. Nemirovsky, et al., J. Polym. Sci. C, vol. 16 (1967), p. 1471–1478 and J. Tabushi, et al., Nippon Kagaku Zasshi, vol. 84 (1963), p. 162–167, report that carbamate groups catalyze the reaction of certain cyclic carbonates and amines. However, the catalysis is slight, about a 30% increase in rates.

SUMMARY OF THE INVENTION

This invention concerns a process for the preparation of hydroxyurethanes, comprising, contacting a cyclic carbonate, a primary amine, and a catalytically effective amount of a base whose conjugate acid has a pKa of about 11 or more.

This invention also concerns a process for the production of hydroxyurethanes by reacting a cyclic carbonate with a primary amine, wherein the improvement comprises, using as a catalyst a catalytically effective amount of a base whose conjugate acid has a pKa of about 11 or more.

DETAILS OF THE INVENTION

A cyclic carbonate herein has its usual meaning, for instance a compound of the formula

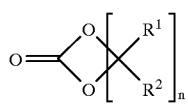

(I)

wherein each $R^1$ and each $R^2$ is independently hydrogen, hydrocarbyl or substituted hydrocarbyl and n is 2 or 3. A preferred cyclic carbonate is

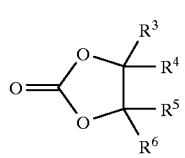

(II)

wherein $R^3$, $R^4$, $R^5$ and $R^6$ are each independently hydrogen, hydrocarbyl or substituted hydrocarbyl. In more preferred cyclic carbonates (individually or collectively) $R^3$ is $Ar^1OCH_2-$, $H_2C=C(CH_3)-C(O)-OCH_2-$ or $H_2C=CH-C(O)-OCH_2-$, $R^4$ is hydrogen, $R^5$ is hydrogen and/or $R^6$ is hydrogen, wherein $Ar^1$ is aryl or substituted aryl. In another preferred form of (II), one of $R^3$, $R^4$, $R^5$ or $R^6$ is attached to a polymer (either directly or through a connecting group), i.e., the cyclic carbonate is a pendant group from a polymer chain.

By a primary amine herein is meant the usual meaning, a compound containing the $-NH_2$ group. It is preferred that this group be bound to an alkyl-type carbon atom, i.e., $R^7R^8R^9CNH_2$ wherein $R^7$, $R^8$ and $R^9$ are each independently hydrogen, hydrocarbyl or substituted hydrocarbyl. In one preferred amine $R^7$, $R^8$ and $R^9$ are each independently hydrogen or alkyl, and more preferably $R^7$ and $R^8$ are hydrogen and $R^9$ is alkyl or cycloalkyl.

When the cyclic carbonate reacts with a primary amine, the product is a hydroxy urethane. For example, reaction of (II) with a primary amine may be written as:

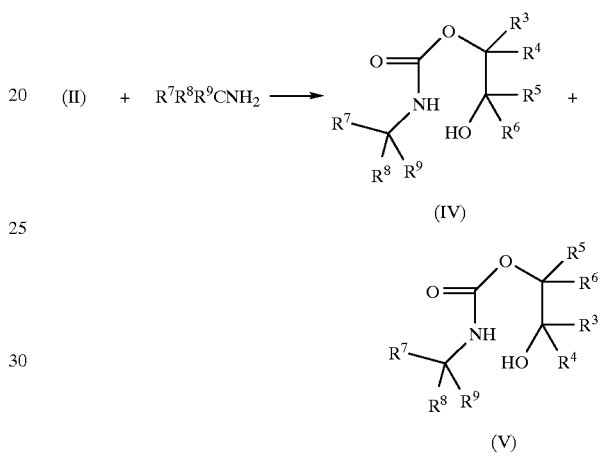

By hydrocarbyl herein is meant a univalent radical containing only carbon and hydrogen. By substituted hydrocarbyl is meant hydrocarbyl substituted with any group that does not interfere with the formation or stability of the cyclic carbonate. Suitable substituent groups include, but are not limited to, halogen, ester, amide, ether and thioether. Substituted aryl is analogous to substituted hydrocarbyl, with the same useful substituents.

The catalyst herein is a base whose conjugate acid has a pKa of about 11 or more, more preferably about 13 or more. One or more bases whose conjugate acid has a pKa of about 11 or more can be used in the process. The pKa is measured in water. For those bases whose conjugate acid has a pKa of about 14 or more, the bascisity can't be measured in water, but the pKa of the conjugate acid will clearly be above 14 in water, because the conjugate acid of the base being measured will be essentially completely formed, along with hydroxyl anion. pKa's, especially for those compounds whose pKa is above about 14, can be measured as described in J. March, "Advanced Organic Chemistry," 3rd Ed., John Wiley & Sons, New York (1985), p. 218–236 and references cited therein, and which is hereby included by reference.

Useful bases are shown in Table 1, along with approximate pKa's (pKa's greater than 14 were measured in solvent systems other than water) taken from literature sources. Preferred bases are t-butoxide, and N,N-bis(trimethylsily)-amide (anion), and t-butoxide is especially preferred. It is also preferred that the base be added in the form of an alkali metal or ammonium salt, and more preferred if it is a potassium salt. The alkali metal or ammonium cations are the counterions of the base anion.

TABLE 1

| Base | pKa |
| --- | --- |
| malononitrile anion | 11.0 |
| alkyl acetoacetate anion | 11.0 |
| methylene disulfone anions | 12.5 |
| trifluoroethoxide | 12.4 |
| diethyl malonate anion | 13.0 |
| N-methyl ethylcarbamate anion | 14.5 |
| methoxide | 15.2 |
| hydroxide | 15.7 |
| ethoxide | 16.5 |
| t-butoxide | 17.0 |
| N-alkylamide anion | 17.0 |
| anions of benzyl alcohols | 16–18 |
| anions of alkyl or aryl ketones | 19–20 |
| diphenylamine anion | 21.0 |
| triphenylmethoxide | 24.0 |
| N,N-bis(trimethylsilyl)amide anion | 28–29 |

The concentration of base present is that needed to be an effective catalyst. By an effective catalytic amount is meant that the rate of reaction of the cyclic carbonate with the amine is at least twice the rate when the base (catalyst) is absent. The rate of reaction is measured by a reaction in a $^1$H Nuclear Magnetic Resonance (NMR) tube under appropriate conditions (see procedure in the Examples). The time to approximately (but the exact same amount of reaction for each sample) half reaction is measured, and to be considered an effective catalyst (base) concentration, the time with the catalyst should be 50% or less (based on the time without catalyst), preferably 25% or less, of the time without catalyst.

A preferred amount of catalyst, based on the moles of the cyclic carbonate present is about 1 mole percent to about 10 mole percent, more preferably about 1.5 mole percent to about 5 mole percent.

Temperature of the process is not critical, a preferred temperature range being about –20° C. to about 120° C., more preferably about 0° C. to about 60° C., and especially preferably about 10° C. to about 40° C. Ratios of reactants are not critical, but in order to most efficiently utilize the ingredients a molar ratio of about 1:1 for the cyclic carbonate and primary amine groups is preferred.

The reaction of cyclic carbonates with primary amines is a known reaction, see for instance British Patent 689,705, U.S. Pat. Nos. 3,072,613 and 4,882,391, and French Patent 1,096,204, all of which are hereby included by reference. In general all that is necessary for the reaction to occur is to bring the reactants into contact, as in solution, or if one or both of the primary amine and carbonate are liquids, without solvent for a period of time sufficient to carry out the reaction.

Polymers that contain cyclic carbonate groups are especially useful since they may be crosslinked by multifunctional compounds that can react with the cyclic carbonate group. Multifunctional amines are particularly desirable in this respect, since upon reaction with the cyclic carbonate urethane groups are formed. Urethane groups are desirable in polymers for certain uses; for example, in coatings urethane groups tend to impart certain improved properties such as gloss, impact resistance, adhesion and toughness.

The cyclic carbonate groups can be introduced into polymers by being part of polymerizable monomers. For instance glycidyl (meth)acrylate may be reacted with $CO_2$ to form the compound

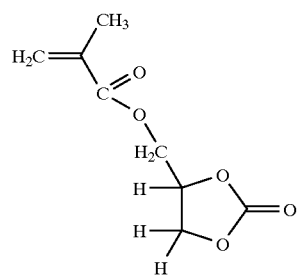

(III)

which may be free radically copolymerized with other (meth)acrylates to form a copolymer which may be crosslinked with a di- (or higher) functional primary amine or a primary amine containing polymer. Such a cyclic carbonate containing polymer preferably contains an average of 2 or more cyclic carbonate groups per polymer molecule. Conversely, a polymer containing primary amine groups may be crosslinked by a compound containing two or more cyclic carbonate groups or a polymer containing cyclic carbonate groups. In both instances, the crosslinks contain desirable urethane groups.

In the catalyzed process described herein the catalyst may be premixed with either the polymer or crosslinking compound, and then the polymer and crosslinking compound (and the catalyst) mixed with each other, and the polymer will eventually crosslink. If meant for a coating, the mixture of the polymer crosslinking agent and catalyst may be applied in a normal manner (e.g., spraying or brushing) and upon standing at ambient conditions the polymeric coating will crosslink. Other ingredients normally present in such coatings can also be present, such as pigments, dyes, antioxidants, reflective agents, dispersants, etc.

Coatings which are crosslinked by the catalyzed process described herein are especially useful for transportation vehicles such as airplanes, automobiles, trucks and railroad cars. They are especially suitable for refinish operations, i.e., repainting of a surface after the coated object has been in service for some time period. The coatings may be applied without the need for baking, as is often done when the transportation vehicle is first manufactured. Since urethane linkages are produced without the uncrosslinked coating containing isocyanate groups, (potential) toxicity problems caused by isocyanate containing compounds are avoided.

EXAMPLES 1–8 AND COMPARATIVE EXAMPLE A

All of these Examples and Comparative Example were done by the same general procedure.

A solution, "A", of 0.2654 g of 4-[(pivaloyloxy)methyl]-1,3-dioxolan-2-one and 0.044 g of durene (as an NMR internal standard) was prepared in 0.275 ml of THF-d$_8$ (tetrahydrofuran). A solution, "B", was prepared from 86.5 μl of N-butylamine (8.75×10$^{-4}$ mole) and 25 μl of THF-d$_8$. Then 360 μl of solution "A" (8.75×10$^{-4}$ mole cyclic carbonate) and all of solution "B" were carefully layered into an NMR tube. The 25 μl of THF-d$_8$ was added to the tube, followed by a solution of 26.3 μl of 1.0 M potassium tert-butoxide in THF (3 mole % KO-t-Bu) was then added to the NMR tube and the whole mixed just prior to taking the NMR spectrum.

NMR spectra were taken on a GE Omega® 300 spectrometer operating at 300.275 MHz, relative to a tetramethylsilane internal standard and are given in ppm. The integrated NMR values observed and used for computing the concentration of starting amine (which was equal to starting cyclic carbonate), a, and the resulting urethane, b, were located at δ=2.58 ppm for the N-methylene group of the N-butylamine, and δ=3.03 ppm for the N-methylene group of the resulting urethane. The relative decrease in the concentration of the amine at a given time was calculated as a/(a+b).

Table 2 shows the decrease in butylamine concentration with time relative to the total amine plus urethane concentration when the reaction was catalyzed by 3 mol % KO-t-Bu. For comparison, the same reaction run without addition of catalyst (Comparative Example A) is also given. The time given is taken from the time of initial mixing of the components.

TABLE 2

| Comp. Ex. A No Catalyst | | Ex. 6 3 mole % KO-t-Bu | |
| --- | --- | --- | --- |
| Rel. Fraction Amine Remaining | Time (min) | Rel. Fraction Amine Remaining | Time (min) |
| 0.96 | 6 | 0.36 | 1 |
| 0.80 | 39 | 0.18 | 9 |
| 0.65 | 72 | 0.13 | 17 |
| 0.52 | 105 | 0.11 | 25 |
| 0.46 | 138 | 0.088 | 33 |
| 0.38 | 171 | 0.078 | 41 |
| 0.32 | 204 | 0.066 | 49 |
| 0.28 | 237 | 0.056 | 62 |
| 0.27 | 270 | 0.052 | 75 |
| 0.23 | 333 | 0.045 | 88 |
| 0.20 | 396 | 0.041 | 101 |
| 0.17 | 459 | 0.038 | 114 |
| 0.16 | 522 | 0.036 | 126 |
| 0.14 | 585 | 0.036 | 139 |
| 0.13 | 648 | 0.030 | 152 |
| 0.11 | 771 | 0.030 | 165 |
| 0.098 | 894 | 0.028 | 188 |
| 0.086 | 1017 | 0.026 | 211 |

All of the other Examples were run in the same manner except for varying and/or amount of catalyst present. Results for all of the Examples are shown in Table 3.

TABLE 3

| | | Time (min)[b] | | | | | |
| --- | --- | --- | --- | --- | --- | --- | --- |
| Example | Catalyst[a] | 0 | 15 | 30 | 45 | 60 | 120 |
| A | none | 1.00 | 0.94 | 0.86 | 0.77 | 0.69 | 0.49 |
| 1 | 1% KO-t-Bu | 1.00 | 0.94 | 0.86 | 0.77 | 0.69 | 0.49 |
| 2 | 10% aceto | 1.00 | 0.74 | 0.66 | 0.56 | 0.52 | 0.38 |
| 3 | 1.5% KO-5-Bu | 1.00 | 0.38 | 0.28 | 0.24 | 0.20 | 0.14 |
| 4 | 10% silyl | 1.00 | 0.30 | 0.17 | 0.12 | 0.08 | 0.04 |
| 5 | 2% KO-t-Bu | 1.00 | 0.20 | 0.13 | 0.09 | 0.07 | 0.04 |
| 6 | 3% KO-t-Bu | 1.00 | 0.14 | 0.09 | 0.07 | 0.06 | 0.04 |
| 7 | 5% KO-t-Bu | 1.00 | 0.11 | 0.05 | 0.03 | 0.02 | 0.01 |
| 8 | 10% KO-t-Bu | 1.00 | 0.05 | 0.02 | 0.01 | 0.00 | 0.00 |

[a]KO-t-Bu is potassium t-butoxide, aceto is tetramethylammonium ethyl 2-acetoacetate, and silyl is potassium (bis)trimethylsilylamide. Percents are mole percent based on cyclic carbonate
[b]Numbers given are relative (to time zero) amounts of amine remaining at the given time

What is claimed is:

1. A process for the preparation of hydroxyurethanes, comprising, contacting, at a temperature of 10° C. to about 40° C., a cyclic carbonate, a primary amine, and a catalytically effective amount of a base whose conjugate acid has a pKa of about 11 or more.

2. A process for the production of hydroxyurethanes, by reacting a cyclic carbonate with a primary amine, wherein the improvement comprises, using as a catalyst a catalytically effective amount of a base whose conjugate acid has a pKa of about 11 or more, said process conducted at a temperature of 10° C. to about 40° C.

3. The process as recited in claim 1 or claim 2 wherein said cyclic carbonate is

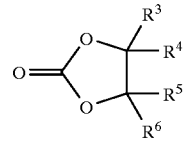

(II)

wherein $R^3$, $R^4$, $R^5$ and $R^6$ are each independently hydrogen, hydrocarbyl or substituted hydrocarbyl.

4. The process as recited in claim 1 or 2 wherein said cyclic carbonate or said primary amine is part of a polymer, or said primary amine is part of a polymer and said cyclic carbonate is part of another polymer.

5. The process of claim 3 wherein $R^3$ is selected from the group consisting of $Ar^1OCH_2$—, $H_2C$=$C(CH_3)$—$C(O)$—$OCH_2$— and $H_2C$=$CH$—$C(O)$—$OCH_2$—, $R^4$ is hydrogen, $R^5$ is hydrogen and/or $R^6$ is hydrogen, wherein $Ar^1$ is aryl or substituted aryl.

6. The process as recited in claim 4 wherein said polymer is crosslinked while said process is being carried out.

7. The process as recited in claim 6 wherein said polymer is part of a coating on a substrate.

8. The process as recited in claim 1 or claim 2 wherein a counterion to said base is an alkali metal cation or an ammonium ion.

9. The process as recited in claim 1 or claim 2 wherein said base is t-butoxide.

10. The process as recited in claim 9 wherein a counterion for said t-butoxide is potassium.

11. The process as recited in claim 1 or 2 wherein said primary amine is $R^7R^8R^9CNH_2$ wherein $R^7$, $R^8$ and $R^9$ are each independently hydrogen, hydrocarbyl or substituted hydrocarbyl.

12. The process as recited in claim 1 or 2 wherein said primary amine is $R^7R^8R^9CNH_2$ wherein $R^7$, $R^8$ and $R^9$ are each independently hydrogen or alkyl.

* * * * *